United States Patent
Saus et al.

(10) Patent No.: US 8,478,609 B2
(45) Date of Patent: Jul. 2, 2013

(54) SYSTEM AND METHOD FOR PREEMPTIVE DETERMINATION OF THE POTENTIAL FOR AN ATYPICAL CLINICAL EVENT RELATED TO THE ADMINISTERING OF MEDICATION

(75) Inventors: Douglas Michael Saus, Platte City, MO (US); Carrie Jeanne Vanzant, Pleasant Valley, MO (US); Russell William Webb, Liberty, MO (US); Kevin John Winkel, Kansas City, MO (US)

(73) Assignee: Cerner Innovation, Inc., Lenexa, KS (US)

( * ) Notice: Subject to any disclaimer, the term of this patent is extended or adjusted under 35 U.S.C. 154(b) by 0 days.

(21) Appl. No.: 13/343,509

(22) Filed: Jan. 4, 2012

(65) Prior Publication Data
US 2013/0006651 A1    Jan. 3, 2013

Related U.S. Application Data

(62) Division of application No. 10/748,046, filed on Dec. 30, 2003, now Pat. No. 8,095,379.

(51) Int. Cl.
*G06Q 10/00* (2012.01)
*G06Q 50/00* (2012.01)

(52) U.S. Cl.
USPC .................................... 705/2; 705/3

(58) Field of Classification Search
USPC ........................................... 705/2–3
See application file for complete search history.

(56) References Cited

U.S. PATENT DOCUMENTS

| 5,842,173 | A | * | 11/1998 | Strum et al. | 705/2 |
| 5,845,255 | A | * | 12/1998 | Mayaud | 705/3 |
| 6,317,719 | B1 | * | 11/2001 | Schrier et al. | 705/2 |
| 2002/0095313 | A1 | * | 7/2002 | Haq | 705/2 |

FOREIGN PATENT DOCUMENTS

WO    WO 9310851 A1 * 6/1993

* cited by examiner

*Primary Examiner* — Joseph Burgess
(74) *Attorney, Agent, or Firm* — Shook, Hardy & Bacon LLP

(57) ABSTRACT

Systems and methods provide for the preemptive determination of the potential of atypical clinical event occurrence related to administering of medications to a person. One method involves receiving a list of possible medications that may be administered to the person during a medical procedure. Subsequently, the medication list is compared to information in the person's medical record. Based on this comparison, a determination is made as to whether one or more matches exist between any of the medications included in the list and the medical record information, the match relating to the potential of an atypical clinical event occurring if the associated medication were to be administered to the person. If a match in fact exists, a response is outputted relating to each match.

7 Claims, 7 Drawing Sheets

| DECISION SUPPORT | | | | | DRUG REFERENCE | EDUCATION LEAFLET | REFERENCE |
|---|---|---|---|---|---|---|---|
| IDENTIFIED ORDER | | | | | | | GRIFFITH, JEFF |
| AMPICILLIN | | | | | | | |

SHOW: ALL

| STATUS | TYPE | SEVERITY | OVERRID... | NAME |
|---|---|---|---|---|
| ORDER | Ⓐ | | | AMPICILLIN |
| | Ⓓ | | | GENTAMICIN |
| | Ⓕ | | | FOOD |

40 — (top of form)
42 — (order table)

AMPICILLIN [____] SEARCH

AMPICILLIN

PHARMACOLOGY, WARNINGS, PREGNANCY, LACTATION, SIDE EFFECTS

PHARMACOLOGY (TOP)

PHARMACOLOGY: AMPICILLIN IS A SEMISYNTHETIC PENICILLIN. LIKE OTHER PENICILLINS, AMPICILLIN INHIBITS BACTERIAL CELL WALL SYNTHISIS. AMPICILLIN HAS ACTIVITY AGAINST GRAM-POSITIVE AND SOME GRAM-NEGATIVE ORGANISMS, INCLUDING ESCHERICHIA COLI, SALMONELLA, PROTEUS MIRABILIS, HAEMOPHILUS INFLUENZAE, AND NEISSERIA GONORRHOEAE. AMPICILLIN IS APPROVED BY THE FDA FOR USE IN THE TREATMENT OF UPPER AND LOWER RESPIRATORY TRACT INFECTIONS, COMPLICATED AND UNCOMPLICATED URINARY TRACT INFECTIONS, OSTEOMYELITIS, MENINGITIS, ENDOCARDITIS, AND PERITONITIS. AMPICILLIN IS ALSO APPROVED FOR USE IN SOME BACTERIAL ENDOCARDITIS PROPHYLACTIC REGIMENS AS RECOMMENDED BY THE AMERICAN HEART ASSOCIATION. ALTHOUGH NOT APPROVED BY THE FDA, AMPICILLIN HAS BEEN USED FOR PROPHYLAXIS AGAINST GROUP B STREPTOCOCCAL INFECTIONS IN OBSTETRICAL PATIENTS.

WARNINGS (TOP)

INTRATHECAL INJECTION IS CONTRAINDICATED BECAUSE IT MAY INDUCE POTENTIALLY FATAL ENCEPHALOPATHY. PSEUDOMEMBRANOUS

46 — (reference pane)

PREVIOUS OVERRIDE REASON: [____]
CURRENT OVERRIDE REASON: [____] FREE TEXT  ☐ APPLY TO

AMPICILLIN – GENTAMICIN (INTERACTION)

AMPICILLIN GENAMICIN: MODERATE ADJUST DOSING INTERVAL: AMPICILLIN MAY INACTIVATE AMINOGLYCOSIDES IN VIVO AND IN VITRO. THE MECHANISM IS COMPLEXATION WITH THE AMINOGLYCOSIDE. TYPICALLY, THIS EFFECT IS

44 — (interaction pane)

☐ REMOVE IDENTIFIED ORDER                    OK

SYSTEM AND METHOD FOR PREEMPTIVE DETERMINATION OF THE POTENTIAL FOR AN ATYPICAL CLINICAL EVENT RELATED TO THE ADMINISTERING OF MEDICATION

CROSS-REFERENCE TO RELATED APPLICATIONS

This application is a divisional patent application of U.S. application Ser. No. 10/748,046, filed Dec. 30, 2003, scheduled to be issued as U.S. Pat. No. 8,095,379 on Jan. 10, 2012, entitled "SYSTEM OF METHOD FOR PREEMPTIVE DETERMINATION OF THE POTENTIAL FOR AN ATYPICAL CLINICAL EVENT RELATED TO THE ADMINISTERING OF MEDICATION," herein incorporated by reference.

STATEMENT REGARDING FEDERALLY SPONSORED RESEARCH OR DEVELOPMENT

None.

BACKGROUND OF THE INVENTION

In the health care industry, there is a desire to increase safety in the process of administering medications (i.e., drugs or pharmaceuticals) to patients. Recent studies have shown that adverse drug reactions (ADRs), such as drug-drug interactions and drug allergy reactions, occur at an alarming rate. For instance, the Institute of Medicine reported that an estimated 106,000 deaths occurred in 1994 due to ADRs, and more than 2,000,000 hospitalized patients experienced serious, if not fatal, ADRs. Lazarou J. et al., *Incidence of adverse drug reactions in hospitalized patients: a meta—analysis of prospective studies*, J. Am. Med. Assn. 1998: 279: 1200-1205. While many of these reactions were attributable to procedural errors, a significant percentage of these reactions were due to inadequate or incomplete information regarding the likely response a particular patient would have to the associated medication.

Sometimes the healthcare worker (e.g., nurse, anesthesiologist, etc.) administering the drug will have a patient's medical record or "chart" available for review prior to taking such action; the medical record includes, for example, information about drugs the patient is currently taking (including vitamins and other natural and synthetic remedies) or allergies to drugs that the patient is known to have. But even if this information is available, the worker still must consult another set of information—specifically pharmacological information regarding drug-drug interactions—to determine whether drugs the patient has already taken would react negatively with a drug to be administered. This sort of information "look-up" or "cross-checking" is subject to human error, and is time consuming, thus reducing efficiency in the delivery of health care services while providing only a moderate level of ADR avoidance. Moreover, such cross-checking becomes increasingly complex when multiple drugs are to be considered as candidates for administration to a patient.

BRIEF SUMMARY OF THE INVENTION

Systems and methods are implemented that facilitate preemptive determination of the potential for an atypical clinical event occurrence related to the administering of a medication to a person. In this way, incidents of ADRs and other atypical clinical events may be reduced and patient safety improved.

In one aspect of the invention, a method in a computing system provides for preemptive determination of the potential for atypical clinical event occurrence related to the administering of one or more medications to a person having an electronic medical record. The method includes receiving a list of possible medications to be administered to the person prior to or during a medical procedure. Subsequently, the medication list is compared to information in the person's medical record. Based on this comparison, a determination is made as to whether one or more matches exist between any of the medications included in the list and the medical record information, the match relating to the potential of an atypical clinical event occurring if the associated medication were to be administered to the person. If a match exists, a response is outputted relating to each match.

In yet another aspect, a computing system provides preemptive determination of the potential for atypical clinical event occurrence related to the administering of a medication to a person having an electronic medical record. A receiving component of the system receives a list of possible medications to be administered to the person prior to or during a medical procedure. This medication list is then taken by a comparing component for comparison with information in the person's medical record. Based on this comparison, a determination is made as to whether one or more matches exists between any of the medications included in the list and the medical record information, by a determining component. Each match relates to the potential of an atypical clinical event occurring if the associated medication were to be administered to the person. An outputting component then outputs a response relating to each of the matches.

Additional advantages and novel features of the invention will be set forth in part in a description which follows, and in part will become apparent to those skilled in the art upon examination of the following, or may be learned by practice of the invention.

BRIEF DESCRIPTION OF THE SEVERAL VIEWS OF THE DRAWING

FIG. 5 illustrates a decision support window;
FIG. 6 illustrates a medication selection window.

DETAILED DESCRIPTION OF THE INVENTION

The present invention includes systems and methods for preemptive determination of the potential for atypical clinical event occurrence related to the administering of one or more medications to a person having an electronic medical record. These systems and methods function such that the health care worker is made aware of risks to the patient prior to administering one or more medications. This allows for selection of alternative medications, if desired, to reduce the risk of the occurrence of atypical clinical events, such as ADR's.

Figure 1:
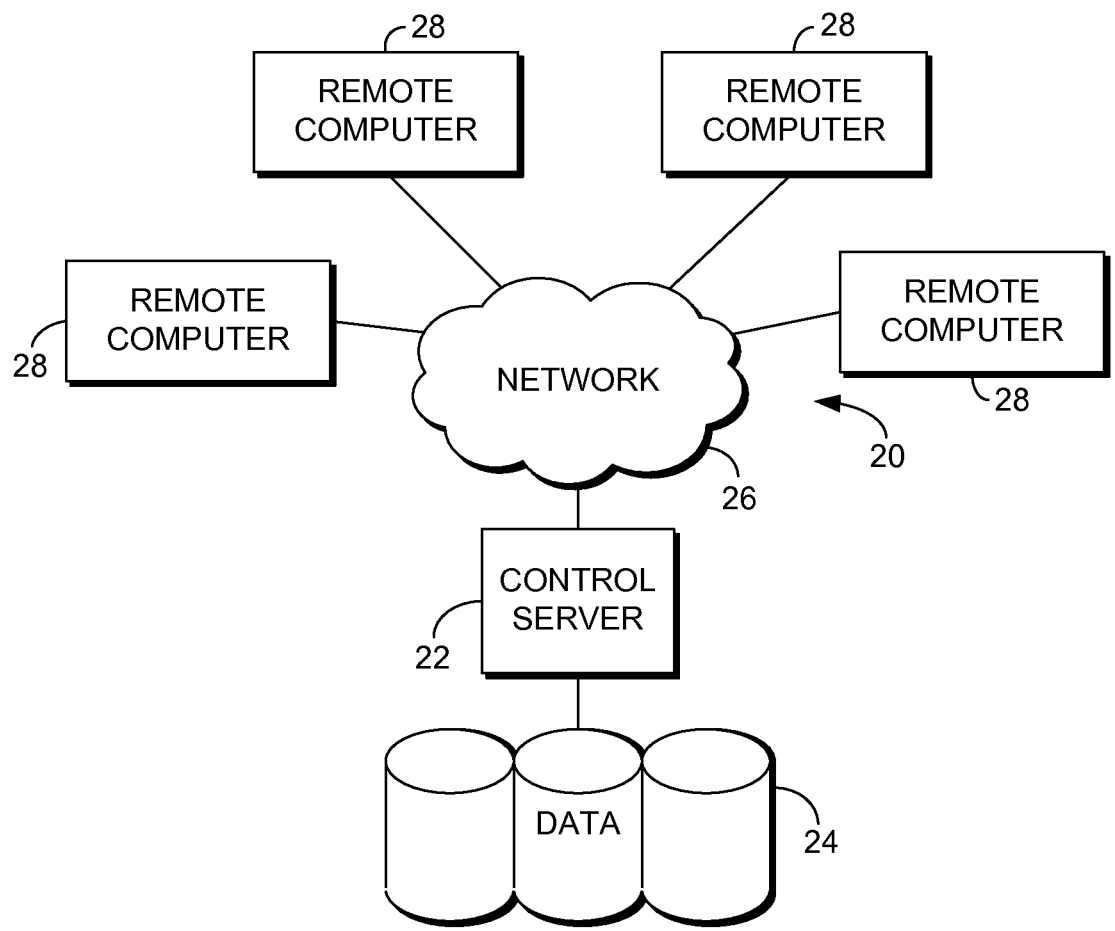
FIG. 1 is a schematic diagram of a suitable computing system environment for use in implementing the present invention.

FIG. 1 illustrates an example of a suitable medical information computing system environment 20 on which the invention may be implemented. The medical information computing system environment 20 is shown merely to facilitate understanding of the invention, and is only one example of a suitable computing environment. Likewise, the computing system environment 20 is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held (e.g., PDAs) or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF (e.g., Bluetooth), infrared, optical and other wireless media. Combinations of any of the above should also be included within the scope of computer readable media.

The computer storage media, including database cluster 24, discussed above and illustrated in FIG. 1, provide a storage of computer readable instructions, data structures, program modules, and other data for server 22. As an example, database cluster 24 may include one or more any type of database, such as relational, hierarchical, object-oriented, and/or the like, and may be organized in any suitable manner, including as data tables or lookup tables.

Server 22 may operate in a computer network 26 using logical connections to one or more remote computers 28. Remote computers 28 can be located at a variety of locations in a medical environment, for example, but not limited to, hospitals, other inpatient settings, pharmacies, a clinician's office, ambulatory settings, testing labs, medical billing and financial offices, hospital administration, and a patient's home environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, and the like. The remote computers may also be physically located in non-traditional medical care environments so that the entire health care community is capable of integration on the network. Remote computers 28 may be a personal computer, hand-held (e.g., PDAs) or laptop device, cellular phone, kiosk, server, router, a network PC, a peer device or other common network node, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone (e.g., using voice recognition techniques), satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention. The systems and methods of the present invention are also described as being implemented in a WINDOWS operating system operating in conjunction with a comprehensive healthcare network or system; however, one skilled in the art would recognize that such systems and methods can be implemented in any system supporting the receipt and processing of clinical agent information or genetic test results.

Figure 2:
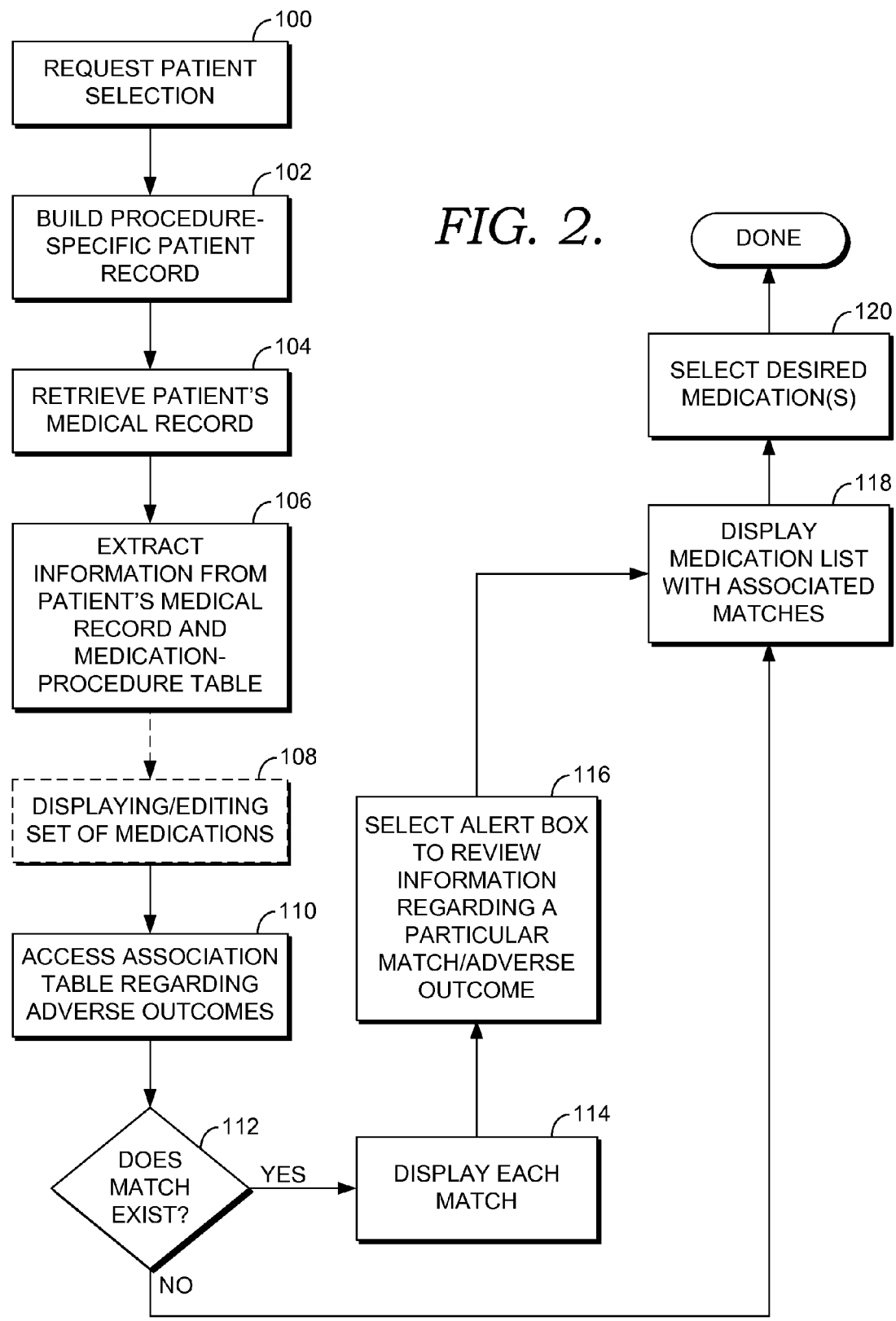
FIG. 2 is a flow diagram illustrating one method for providing information regarding the potential for atypical clinical event occurrence relating to administering a medication to a patient.

Operation of one embodiment of the system of the present invention for informing a user of the potential for atypical clinical event occurrence when administering medication to a patient is shown in FIG. 2. The term "atypical clinical event" refers to any non-responsive or adverse event that may result from a patient receiving medication, examples of which include drug-drug interactions (e.g., one medication or drug impeding the chemical activity and/or the absorption of another drug), drug-food interactions, drug-gene interactions and drug-allergy reactions. The term "patient" refers to a person that is receiving medication in any location in a medical environment (e.g., hospitals or other inpatient or outpatient settings, a clinician's office, ambulatory settings, testing labs, patient's home environment, or in any other setting).

The system interacts with a pre-existing electronic medical record (EMR) of a patient, which may contain information such as the medications the patient is currently taking (including dosage amounts and when the medications were delivered), foods the patient is consuming (and when they were consumed), allergies to medications that the patient is known to have and/or genetic test results for the patient, and which may be stored on a unified healthcare network. However, the term "electronic medical record" should not be interpreted to be limited to any type of computer-readable format or record, but includes any data structure containing information relative to a specific patient and from which information may be extracted by the system of the present invention. The method of use of the system may also include steps requiring authorization of the user to access particular patient information and similar security measures known by those of skill in the art.

The system embodiment shown in FIG. 2 is also configured to interact with one or more pre-built medication-procedure tables, which maintain a standard list or set of medications—optionally, with a recommended dosage amount for each—that may be administered during a specific type of medical procedure or treatment. For example, one type of medical procedure may include a grouping of many individual procedures (e.g., any procedure where anesthesia is used), or may include a specific kind of surgical procedure (e.g., appendectomy); however, it should be appreciated that a medical procedure may also be any other type of procedure (a radiologic or oncologic medical procedure, as other examples). Additionally, the medication-procedure tables may include a universal set of medications that may be administered regardless of the type of medical procedure or treatment, such that the universal set is effectively associated with all procedures (e.g., a set of medications determined to be of a particularly dangerous nature when administered in any type of medical procedure). Each medication may also carry a type or category designation (e.g., antibiotic, antidrhythmic, etc.) within the medication-procedure tables. Preferably, the medication-procedure tables are stored in the memory of the system such as in the database cluster 24.

Thus, clinicians can use the medication-procedure tables as a template for the medications that are oftentimes administered to a patient in a given medical procedure (or medications that may be administered regardless of the type of procedure). Additionally, the medication-procedure tables may be edited or updated at any time as standard protocol is changed for what specific medications are optional for administering to a patient during a given type of medical procedure.

Figure 3:
FIG. 3 illustrates a patient selection window.

In a first step, the system requests the selection of the particular patient for which the pre-built set of possible medications to be administered is to be checked in step 100. By way of example, as seen in FIG. 3, an exemplary user interface window 30 of the conventional kind is shown for requesting patient selection. Preferably, displaying of window 30 and patient selection is conducted at one of the remote computers 28 and transmitted to the control server 22 via the network 26. Any of a number of input devices, displays, and techniques may also be utilized at this step of the method and in each of the subsequent steps wherein user input is received and/or information displayed.

The patient may be selected from a list of patients extracted from; patient-procedure entries stored in the unified healthcare network. Each patient-procedure entry includes information about a patient and a corresponding medical procedure the patient is scheduled to undergo, for example, the patient's name, social security number, type of procedure to undergo, location where the procedure is to take place, or any other related information. Information contained in the patient-procedure entries is typically gathered at events such as during a pre-operative meeting, but may be gathered at any other time prior to system step 100.

The patient list may be displayed on the user interface window 30 in a variety of ways. For instance, the clinician operating the system may view a scrollable table 32 of the patient-procedure entries—in this case, each relating to a surgical procedure—and select the desired entry from the list with an input device (e.g., a mouse), or may select a patient by inputting information in one of the associated text boxes 34 of window 30 and searching for the patient by information such as an assigned case number, the anesthesiologist treating the patient during the procedure, etc.

Upon selection of the patient, a procedure-specific patient record is built by the system of the present invention at step 102, which may be stored in the memory of the system such as in the database cluster 24. The procedure-specific patient record incorporates the information from the selected patient-procedure entry.

Now having the particular patient identified by the system, the patient's existing electronic medical record (EMR) is retrieved from the unified healthcare network by the system at step 104. Information is then extracted from the electronic medical record and from the pre-built medication-procedure table for the particular medical procedure chosen, at step 106. Preferably, the information from the patient's electronic medical record includes medications the patient is taking or has recently taken (including pharmaceuticals, vitamins, natural and synthetic remedies and the like), foods that have been ingested/consumed, medication allergies and/or genetic test results, and information from the table includes the set of medications associated with the particular procedure. This extracted information is preferably incorporated into the procedure-specific patient record such that this record displays for the clinician desired information about the patient and the scheduled medical procedure. Additionally, the extracted information may also include patient information such as their age or weight, which may be relevant to the dosage of the medications in the medication-procedure tables in terms of the likelihood of atypical clinical event occurrence. Alternatively, the clinician may themselves enter onto the system the patient-specific characteristics including patient age and/or weight instead of such information being extracted from the associated patient medical record.

One optional step of the system, step 108, includes displaying of the set of medications for the particular medical procedure chosen. This allows the clinician to edit the set (e.g., add or remove medications) as they desire and incorporate the edited medication set into the procedure-specific patient record.

At step 110, the system takes the extracted information from step 106 (and optionally step 108), and accesses a drug-drug, drug-food association table to make a comparison regarding the potential for atypical clinical event occurrence if one or more of the medications are administered to the patient. The association table may be maintained in the memory of the system such as in database cluster 24, or elsewhere within the system or within the comprehensive healthcare network. For example, the association table may be accessed via a global computer network such as the Internet rather than being stored in database cluster 24 as described above with reference to one preferred embodiment. One example of a suitable association table is the drug-drug and/or drug-food association table maintained by Cerner Multum. The table includes information regarding adverse affects caused by two or more specific medications interacting with one another within a person, or by a medication and a food interacting within a person. For instance, one of the aforementioned interactions may include the magnification of the effects of the administered medication beyond what is desired, or one medication impeding the chemical activity and absorption of another medication, purely as examples. The table may further contain information on the severity of the adverse effects relative to the dosage of the administered medication and the age or weight of the person receiving the medication. As appreciated by those of skill in the art, a particular medication may interact with more than one other medication, or with more than one type of food. Additionally, as more information about drug-drug and drug-food interactions is learned, this information may be added to the particular drug-drug and/or drug-food association table used in conjunction with the present invention.

At step 112, a determination is made as to whether one or more matches exists between the medication information in the medication-procedure table and the patient medical record information. This determination involves both (a) drug-allergy reactions matched by direct comparison between the medication-procedure table and the patient's medical record information, (b) drug-drug and drug-food interactions matched by comparison between the medication-procedure table and the patient's medical record information through the drug-drug and/or drug-food association table. As one example, if the patient is undergoing a medical procedure where the medication Ampicillin is one choice of antibiotic that may be administered, step 116 determines both if the specific patient is known to be allergic to Ampicillin and, through consulting the association table, whether Ampicillin will cause an adverse outcome through a drug-drug or drug-food interaction with a medication or food the patient has consumed or taken. The matches relating to drug-drug and drug-food interactions may also depend on the dosage of the medication to be administered, such that the severity of the adverse outcome may be gauged.

Figure 4:
FIG. 4 illustrates a medication alert window.

If one or more matches are found, then at step 114, the system outputs a response notifying the clinician of each match. FIG. 4 shows one exemplary response relating to a drug-drug interaction match between the antibiotics Gentamicin and Ampicillin. The response is in the form of a medication alert window 36 provided on a display of the system. The window 36 presents a number of alert boxes 38, preferably one for each match found by the system. In this representative example, only one match was found, therefore only one alert box is generated by the system. Each alert box 38 may include, for example, the specific medication that may be administered involved in the particular match, the category of the medication(s) involved in the match (in this representative example, antibiotics), the type of match (which may be denoted by the initials "D" for drug-drug, "A" for drug-allergy, "F" for drug-food, and "G" for drug-gene), and the predicted severity of the associated atypical clinical event (e.g., mild, moderate or severe indicated by arrows or other graphical symbols or audible alerts). The alert box 38 may further include, in addition to the medication that may optionally be administered, the medication or food the patient has ingested/taken, and may also include an indication whether the dose of medication is excessive and could result in an overdosing of the patient (e.g., if the patient is a pediatric patient—as determined from the patient information gathered—and the medication dosage is an adult dosage—based on strength and concentration—as determined from the medication-procedure tables). Additionally, patient information 35 associated with the procedure-specific patient record may be displayed on window 30 or on any other window of the system. This information 35 may include, for example, the patient's name, date of birth, and other personal information, as well as the medical procedure to be performed on the patient and allergies the patient has, and other related information.

Each alert box 38 may be selected by the clinician to view more detailed information about the type of match, at step 116. FIG. 5 shows an exemplary decision support window 40 displayed once an alert box 38 has been selected. In this particular case, the representative alert box (not shown) included Ampicillin as the medication that may be administered, and returned drug-drug, drug-food and drug-allergy matches for the patient. A table 42 lists each match for Ampicillin and displays the type of match (denoted by the initial representative of the match), the severity of the atypical clinical event, and what the medication interacts with (i.e., medication or food the patient has consumed/taken). The clinician may scroll through the table 42 to select a particular match entry, for example, the drug-drug interaction between Ampicillin and Gentamicin, and sub windows 44, 46 display medical, pharmacological or other evidence-based information relating to the match and to the medication that may be administered. Subsequently, the clinician may close the decision support window 40 and select another alert box 38 to view information about other matches.

Figure 6:
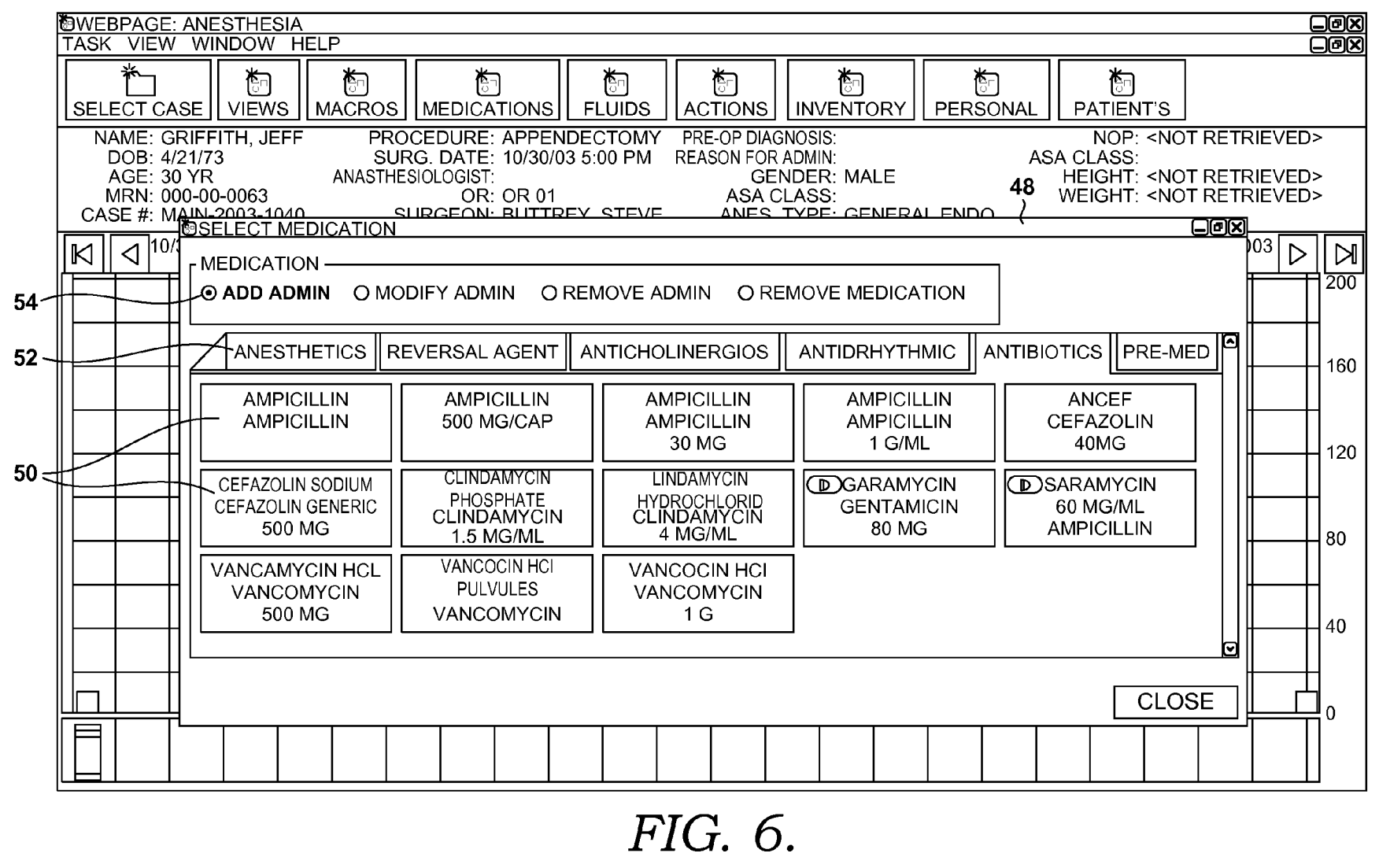

Once the clinician is satisfied that sufficient information about the matches and associated atypical clinical events has been considered, the medication alert window 36 may be closed and the system displays an exemplary select medication window 48 at step 118, and as shown in FIG. 6. Additionally, if no matches were found in step 112, the system moves directly to step 118.

At step 118 the select medication window 48 provides the medications that may be administered (from the medication-procedure table) in medication boxes 50, and is preferably segmented into medication categories (e.g., antibiotics, antidrhythmics, etc.) so that the clinician may select the appropriate medication(s) for administration. Each of the medication categories may be indexed on a tab 52 such that the clinician can move easily between categories to see the medication options. Each medication box 50 lists the medication name, and may also provide the medication trade name, the recommended dosage for the patient (if patient-specific characteristics are known), and the type of match, if any, that was discovered, as well as the predicted severity of the associated atypical clinical event (not shown). In this particular example, medication boxes for the medication Garamycin are shown and include a "D" to indicate a drug-drug interaction as an atypical clinical event if this medication is administered to the patient. The window 48 also provides selection boxes 54 that control the function of user selections made to the medication boxes 50. In other words, the selection boxes 54 modify the function of "clicking" on or otherwise selecting a selected box 50. For instance, the clinician may add or remove a medication to or from the procedure-specific patient record for administration to the patient in association with the selected medical procedure, modify the medication dosage suggested, or remove a specific medication box 50, thereby removing the associated medication from the medication-procedure table such that the medication will not be presented in the future as an option when the associated medical procedure is selected.

At step 120, the clinician, in the select medication window 48, makes the desired medication selections in each medication category to complete the list of medications to be added to the procedure-specific patient record and administered to the particular patient. Thus, the clinician is properly informed of the risks of the occurrence of adverse drug events in the patient and may tailor their medication selection to avoid such risks.

As discussed above, the system embodiment of FIG. 2 may also be applicable to drug-gene interactions. This is useful because of the individual variability in the response to drugs due to the differences in genetic makeup between any two given persons. In one example of operation of the system embodiment of FIG. 2, the medications list for a given medical procedure may be compared with a table of gene variations and associated polymorphisms accessed at system operation step 110. Information from the patient's medical record or other record regarding genetic testing information is also extracted at system operation step 106. Then, at step 112, a determination may also be made as to whether one or more matches exists between the medication information in the medication-procedure table and patient's genetic testing information that would result in an adverse or atypical outcome. Each alert box may include the specific medication that may be administered involved in the particular match, the category of the medication(s) involved in the match (in this representative example, antibiotics), the type of match (such as a "G" for drug-gene), and the predicted severity of the associated atypical clinical event (e.g., mild, moderate or severe indicated by arrows or other graphical symbols or audible alerts). One example of an atypical outcome would be that a given medication may be non-responsive and not provide the patient with the intended benefit. If one or more matches exist, associated responses are outputted in step 114 (e.g., displayed on alert box 38, FIG. 4) along with information related to matches, such as phenotypes, risks, etc.

Figure 7:
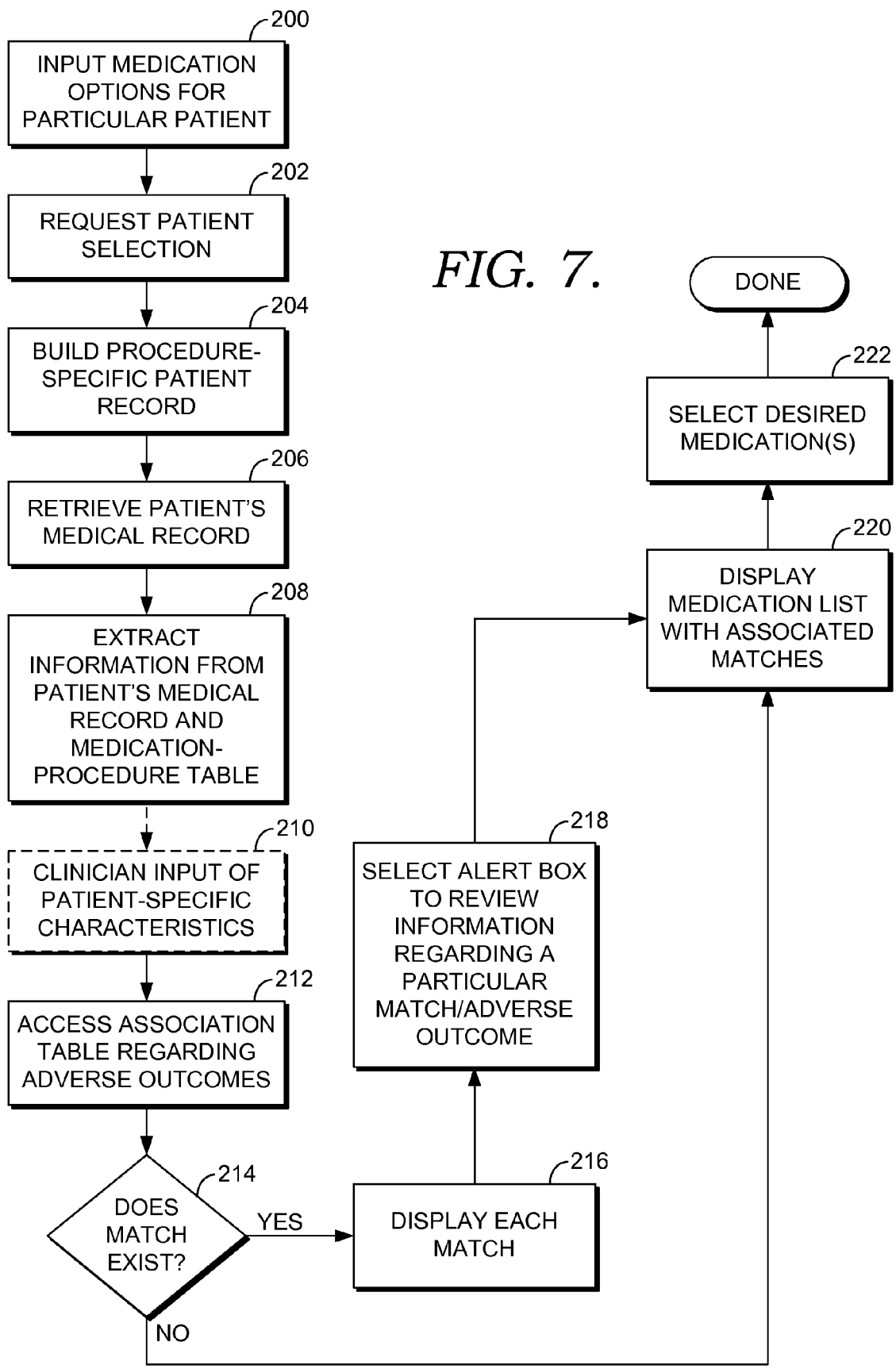
FIG. 7 is a flow diagram illustrating another method for providing information regarding the potential for atypical clinical event occurrence relating to administering medication to a patient.

FIG. 7 shows the operation of another embodiment of the system of the present invention for informing a user of the potential for atypical clinical event occurrence when administering medication to a patient. The system embodiment of FIG. 7 shares some similarities to the embodiment of the system of FIG. 2, but medications that may be administered are gathered relative to a particular patient, not just with respect to a particular medical procedure alone. Also, terms used above to describe the system embodiment of FIG. 2 should be interpreted consistently with respect to the system embodiment shown in FIG. 7.

The operation of the system of FIG. 7 begins with the clinician or other individual inputting into the system medications that may be administered specific to a particular patient undergoing a certain medical procedure or treatment, at step 200, such that a list of medications is generated. Accordingly, patient and procedure identifying information relating to the list is also inputted in this step, some examples of which include the patient's name, social security number, location whether the procedure is to take place, patient-specific characteristics, or any other related information. Still further, other information associated with each medication may also be inputted, such as a dosage amount for the respective medication based on the specific medical procedure to be conducted and/or other factors, and a type or classification designation for the medication.

The gathering of patient/procedure and medication information in step 200 may occur at any time once it is determined that the patient is scheduled to undergo a specific medical procedure (e.g., at a pre-operative meeting). Likewise, this information may be stored as any type of data structure, for example, compiled into a medication-patient table, in the memory of the system (e.g., in database cluster 24), and is preferably inputted into the system at one of the remote computers 28 and transmitted to the control server 22 via the network 26. Any of a number of input devices, displays, and techniques may be utilized at this step of the method and in each of the subsequent steps wherein user input is received and/or information displayed. As with the system of FIG. 2, the term "medical procedure" signifies any type of procedure or treatment; purely as an example, one type of medical procedure would be any procedure where anesthesia is used.

Subsequently, at step 202, when the clinician is ready to determine the potential for atypical clinical event occurrence upon administering drugs to a patient for a given medical procedure, the system requests the selection of the particular patient for which the list of possible medications to be administered is to be checked (e.g., from a list of patients extracted from patient-procedure entries stored in the unified healthcare network). This step is similar to step 104 of the system embodiment of FIG. 2, and patient information may be requested through the exemplary user interface window 30 of FIG. 3 and by use of the scrollable table 32 or text boxes 34 of the window 30 to select a particular patient entry.

Upon selection of the patient, at step 204 the system builds a procedure-specific patient record, which may be stored in the memory of the system such as in the database cluster 24. The procedure-specific patient record incorporates the information from the selected patient entry. Then, at step 206 and having the particular patient identified by the system, the patient's electronic medical record is retrieved from the comprehensive healthcare network by the system. Information is then extracted from the medical record and from the medication-patient table gathered in step 200, at step 208. Preferably, the information from the patient's medical record includes medications the patient is taking or has recently taken, foods that have been ingested/consumed and medication allergies, and information from the table includes a listing of the medications associated with the particular procedure. This extracted information is preferably incorporated into the procedure-specific patient record such that this record displays for the clinician desired information about the patient and the scheduled medical procedure. Also, in the same fashion as the operation of the system embodiment of FIG. 2 in step 106, the extracted information may also include patient information such as their age or weight, which may be relevant to the dosage of the medications in the medication-procedure tables in terms of the likelihood of atypical clinical event occurrence. Alternatively, in step 210, the clinician may themselves enter onto the system the patient-specific characteristics instead of such information being extracted from the associated patient medical record, so that the proper dosage amount may be determined.

Steps 212-222 of the system embodiment of FIG. 7 are essentially identical to steps 110-120 of the system embodiment of FIG. 2, and will merely be briefly summarized herein.

At step 212, the system takes the extracted information from step 208 (and optionally step 210), and accesses a drug-drug and/or drug-food association table to make a comparison regarding the potential of atypical clinical event occurrence if one or more of the medications are administered to the patient, including the severity of any adverse effects. Then, at step 214, a determination is made as to whether one or more matches exists between the medication information in the medication-procedure table and the patient medical record information, which involves both (a) drug-allergy reactions matched by direct comparison between the medication-procedure table and the patient's medical record information, and (b) drug-drug and drug-food interactions matched by comparison between the medication-procedure table and the patient's medical record information through the drug-drug and/or drug-food association table. The matches relating to drug-drug and drug-food interactions may also depend on the dosage of the medication to be administered, such that the severity of the atypical clinical event may be gauged.

If one or more matches are found, the system outputs a response notifying the clinician of each match, at step 216, and as shown in FIG. 4. The medication alert 36 presents the exemplary alert box 38 notifying of the drug-drug interaction match between the antibiotics Gentamicin and Ampicillin. The alert box 38 may include the medication name(s), the category of the medication(s) involved in the match, the type of match, the predicted severity of the associated atypical clinical event, among other information. Patient information 35 associated with the procedure-specific patient record may be displayed on window 30. Additionally, at step 218, selection of the alert box 38 will take the clinician to the exemplary Decision Support window 40 shown in FIG. 5. The table 42 lists each match for Ampicillin (in this particular example) and displays the type of match, the severity of the atypical clinical event, and with what the medication will interact. If the exemplary drug-drug interaction shown, between Ampicillin and Gentamicin, is selected the sub windows 44, 46 display medical or pharmacological information relating to the match and to the medication that may be administered.

Once the clinician is satisfied that they have been presented with sufficient information about the matches and associated atypical clinical events, the medication alert window 36 may be closed and the system displays the exemplary Select Medication window 48 at step 220, and as shown in FIG. 6. Additionally, if no matches were found in step 214, the system moves directly to step 220.

At step 220, the select medication window 48 provides the medications that may be administered (from the medication-patient table) in medication boxes 50, and preferably broken down into medication categories so that the clinician may select the appropriate medication(s) for administration. Each of the medication categories may be indexed on a tab 52 such that the clinician can move easily between categories to see the medication options. Selection boxes 54 may also be provided by the window 48 for controlling the function of user selections made to the medication boxes 50. Then, at step 222, the clinician can make the desired medication selections in each medication category (through window 48) to complete the list of medications to be added to the procedure-specific patient record and administered to the particular patient.

Similar to the system embodiment of FIG. 2, the system embodiment of FIG. 7 may, as well, be applicable to drug-gene interactions within a person. One exemplary operation for the system embodiment would include the comparison of the medication list for a given patient undergoing a medical procedure with a table of gene variations and associated polymorphisms accessed at system operation step 212. Additionally, information from the patient's medical record or other record regarding genetic testing information is also extracted at system operation step 208. A determination may then be made, at step 214, as to whether one or more matches exist between the medication information in the medication list and patient's genetic testing information that would result in an atypical clinical event. In other words, the system determines if the products of the genes are likely to interact with the medications on the list to result in an atypical clinical event. If one or more matches exist, associated responses are outputted in step 216 along with information related to matches (phenotypes, risks, etc).

EXAMPLE

One example of a particular usage of the system embodiments of FIGS. 2 and 7 is with gauging the potential of atypical clinical event occurrence when considering medication options for a surgical procedure where anesthesia is used. As seen in FIG. 3—whether a list of potential medications that may be administered is created for a type of procedure generally (as in the system of FIG. 2) or with respect to a specific patient and procedure (as in the system of FIG. 7)—the patient is searched for in user interface window 30 by the associated operating room, anesthesiologist, starting dates and time for the scheduled medical procedure, or by other identifying information. In this particular case, the anesthesia medication list includes those that are choices for administering to the patient by a clinician, including medications in the categories of antibiotics, antidrhythmics, intubation medications, pre-operative medications, anticholinergics, and reversal agents, among others. Based on the anesthesia medication list, the system returns a match for the drug-drug interaction between garamycin and ampicillin in the alert box 38 of FIG. 4. Selecting the box displays the decision support window 40, which provides information about the associated drug-drug interaction, as well as pharmacology, and warning information related to the selected drug, in this case, ampicillin. The clinician then selects, in the select medication window 48 of FIG. 6, the tab 52 relating to each category of medication that may be administered until all of the proper medication necessary for the surgical procedure are chosen. Here, the clinician is reviewing the medication options for the antibiotics that may be administered, noting that the medication boxes 50 show that Garamycin, in the listed dosage options, may cause a drug-drug interaction with medication this particular patient has taken. Therefore, the clinician should choose one of the other medication boxes 50 to administer a different antibiotic for the patient before or during the medical procedure.

As can be seen, the present systems and methods provide a robust solution for reducing the occurrence of ADR's and other similar atypical clinical events when a patient is to receive certain medications in conjunction with undergoing a medical procedure, such as a surgery. The features of the present invention provide for the customization of a list of medication options that may be chosen from when needed for a specific medical procedure. By checking a meaningful list of medications simultaneous for atypical clinical events, instead of having the user check medications individually, substantial time savings are realized, and the burden on the clinician is reduced, making it more likely that he or she will check all of the medication choices for possible ADR's. At the same time, it should be understood that a clinician may desire to only check certain medications of a group that may be administered to a patient, or a certain family of medications (e.g., antibiotics), with the systems of the present invention, if the clinician is aware that other medications that may be administered will not cause an atypical clinical event to occur.

The systems and methods of the present invention also provide value in clinical situations where medications are not ordered prior to a procedure taking place, but are administered immediately after a clinician deems them necessary (e.g., antibiotics for a trauma patient in an emergency room). In this way, the clinician may check a medication list, and if the system determines that there is no significant risk of an atypical clinical event occurring, the clinician can promptly administer the medication.

Furthermore, since certain changes may be made in the above systems and methods without departing from the scope hereof, it is intended that all matter contained in the above description or shown in the accompanying drawing be interpreted as illustrative and not in a limiting sense. It is also to be understood that the following claims are to cover certain generic and specific features described herein.

What is claimed is:

1. A method in a computing system for preemptive determination of the potential for atypical clinical event occurrence related to the administering of at least one medication to a person having an electronic medical record, the method comprising the steps of:
   accessing medication-procedure tables that maintain specific sets of medications and dosages thereof that are administered for each of a plurality of medical procedures, wherein the medication-procedure tables include a universal set of medications that are particularly dangerous when administered in a variety of medical procedures;
   selecting a list of medications from the medication-procedure tables that are to be administered to the person for a medical procedure scheduled for the person, wherein the medication list includes a specific set of medications and dosages thereof that correspond to the medical procedure and the universal set of medications;
   employing a control server to compare the medication list directly against information extracted from the person's electronic medical record (EMR);
   determining that at least one match exists between any of the selected medications included in the medication list and the EMR information, wherein the at least one match indicates the potential of drug-allergy reactions occurring when the matching medication is administered to the person;
   employing the control server to compare the medication list against the information in the person's EMR a drug-drug association table and a drug-food association table, wherein the drug-drug association table includes information regarding adverse affects caused by medications interacting with each other, and wherein the drug-food association table includes information regarding adverse affects caused by a medication and a food interacting with each other;
   determining that at least one match exists between any of the selected medications included in the medication list and the EMR information upon employing the drug-drug and the drug-food association tables, wherein the match indicates the potential of drug-drug or drug-food reactions occurring upon the selected medication being administered to the person; and
   outputting a response relating to each match.

2. The method of claim 1, wherein the medical procedure includes any medical procedure requiring the use of anesthesia.

3. The method of claim 1, wherein the information in the person's EMR includes a list selected from one of the groups consisting of medications the person is currently taking or has recently taken, foods the person has consumed, the person's allergies to medications and genetic test information for the person.

4. The method of claim 1, wherein the response includes a listing of the match and an associated atypical clinical event, and wherein the atypical clinical event is one selected from the group consisting of a drug-drug interaction, drug-food interaction, drug-allergy interaction and a drug-gene interaction.

5. The method of claim 1, further comprising modifying the medication list by adding or deleting medications from the list prior to comparing the medication list to information in the person's EMR.

6. Non-transitory computer storage media containing computer-executable instructions that, when executed, perform a method for controlling a computing system for preemptive determination of the potential for atypical clinical event occurrence related to the administering of at least one medication to a person having an electronic medical record (EMR), the method comprising the steps of:
   accessing medication-procedure tables that maintain specific sets of medications and dosages thereof that are administered for each of a plurality of medical procedures;
   selecting a list of medications from the medication-procedure tables that are to be administered to the person for a medical procedure scheduled for the person;
   comparing the medication list directly against information extracted from the person's EMR;
   determining that at least one match exists between any of the selected medications included in the medication list and the EMR information, wherein the at least one match indicates the potential of drug-allergy reactions occurring when the matching medication is administered to the person;
   comparing the medication list against the information in the person's EMR a drug-drug association table and a drug-food association table, wherein the drug-drug association table includes information regarding adverse affects caused by medications interacting with each other, and wherein the drug-food association table includes information regarding adverse affects caused by a medication and a food interacting with each other;
   determining that at least one match exists between any of the selected medications included in the medication list and the EMR information upon employing the drug-drug and the drug-food association tables, wherein the match indicates the potential of drug-drug or drug-food reactions occurring upon the selected medication being administered to the person; and outputting a response relating to each match.

7. The computer storage media of claim 6, wherein the medication-procedure tables include a universal set of medications that are particularly dangerous when administered in a variety of medical procedures, and wherein the medication list includes a specific set of medications and dosages thereof that correspond to the medical procedure and the universal set of medications.

* * * * *